United States Patent
Mershin

(10) Patent No.: US 10,364,410 B2
(45) Date of Patent: Jul. 30, 2019

(54) METHODS AND APPARATUS FOR SHIFTED-WAVELENGTH PHOTOSYNTHETIC ENERGY HARVESTING AND BIOMASS PRODUCTION

(71) Applicant: Massachusetts Institute of Technology, Cambridge, MA (US)

(72) Inventor: Andreas Mershin, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

(21) Appl. No.: 15/483,572

(22) Filed: Apr. 10, 2017

(65) Prior Publication Data
US 2017/0298312 A1    Oct. 19, 2017

Related U.S. Application Data

(60) Provisional application No. 62/321,878, filed on Apr. 13, 2016.

(51) Int. Cl.

| | | |
|---|---|---|
| C12M 1/00 | (2006.01) | |
| C12M 1/22 | (2006.01) | |
| C12N 13/00 | (2006.01) | |
| C12N 1/12 | (2006.01) | |
| C12N 1/20 | (2006.01) | |
| C12M 1/36 | (2006.01) | |
| C12M 1/42 | (2006.01) | |

(52) U.S. Cl.
CPC ............ *C12M 23/10* (2013.01); *C12M 31/02* (2013.01); *C12M 35/02* (2013.01); *C12M 41/06* (2013.01); *C12M 41/48* (2013.01); *C12N 1/12* (2013.01); *C12N 1/20* (2013.01); *C12N 13/00* (2013.01)

(58) Field of Classification Search
CPC ..................................................... C12M 1/002
See application file for complete search history.

(56) References Cited

U.S. PATENT DOCUMENTS

| | | | |
|---|---|---|---|
| 8,796,544 B2 | 8/2014 | Mershin et al. | |
| 2008/0274541 A1* | 11/2008 | Selker | B01F 3/04248 435/289.1 |
| 2009/0047722 A1* | 2/2009 | Wilkerson | C12M 21/02 435/173.7 |
| 2016/0002611 A1 | 1/2016 | Mershin et al. | |

OTHER PUBLICATIONS

Croce, R., et al., Natural strategies for photosynthetic light harvesting; published in Nature Chemical Biology, vol. 10, pp. 492-501 (2014).

(Continued)

*Primary Examiner* — Rosanne Kosson
(74) *Attorney, Agent, or Firm* — Norma E. Henderson

(57) ABSTRACT

One or more light sources may apply stimuli to a colony of organisms. The stimuli may include visible and non-visible light. The stimuli, taken together, may tend to favor survival of organisms that are adapted to perform photosynthesis which involves absorbing energy from infrared or ultraviolet light. In some cases, the set of stimuli may include illuminating the entire colony of organisms with green light, illuminating only a first portion of the colony with pulsed ultraviolet light, and illuminating only a second portion of the colony with pulsed infrared light.

13 Claims, 1 Drawing Sheet

(56) References Cited

OTHER PUBLICATIONS

Hill, J., et al., The controversy over the minimum quantum requirement for oxygen evolution; published in Photosynthesis Research, vol. 122, Issue 1, pp. 97-112 (2014).

Johkan, M., et al., Effect of green light wavelength and intensity on photomorphogenesis and photosynthesis in Lactuca sativa; published in Environmental and Experimental Botany, vol. 75, Jan. 2012, pp. 128-133.

Mershin, A., et al., Self-assembled photosystem-I biophotovoltaics on nanostructured TiO2 and ZnO; published in Scientific Reports 2, Article No. 234 (2012).

Osborne, B., et al., The minimum photon requirement for photosynthesis; published in The New Phytologist, vol. 106, Issue 4, pp. 631-644 (1987).

Pullerits, T., et al., Beatings in electronic 2D spectroscopy suggest another role of vibrations in photosynthetic light harvesting; published in Proceedings of the National Academy of Sciences of the United States of America, vol. 110, No. 4, pp. 1148-1149 (Jan. 2012).

Tiwari, V., et al., Electronic resonance with anticorrelated pigment vibrations drives photosynthetic energy transfer outside the adiabatic framework; published in Proceedings of the National Academy of Sciences of the United States of America, vol. 110, No. 4, pp. 1203-1208 (Jan. 2012).

\* cited by examiner

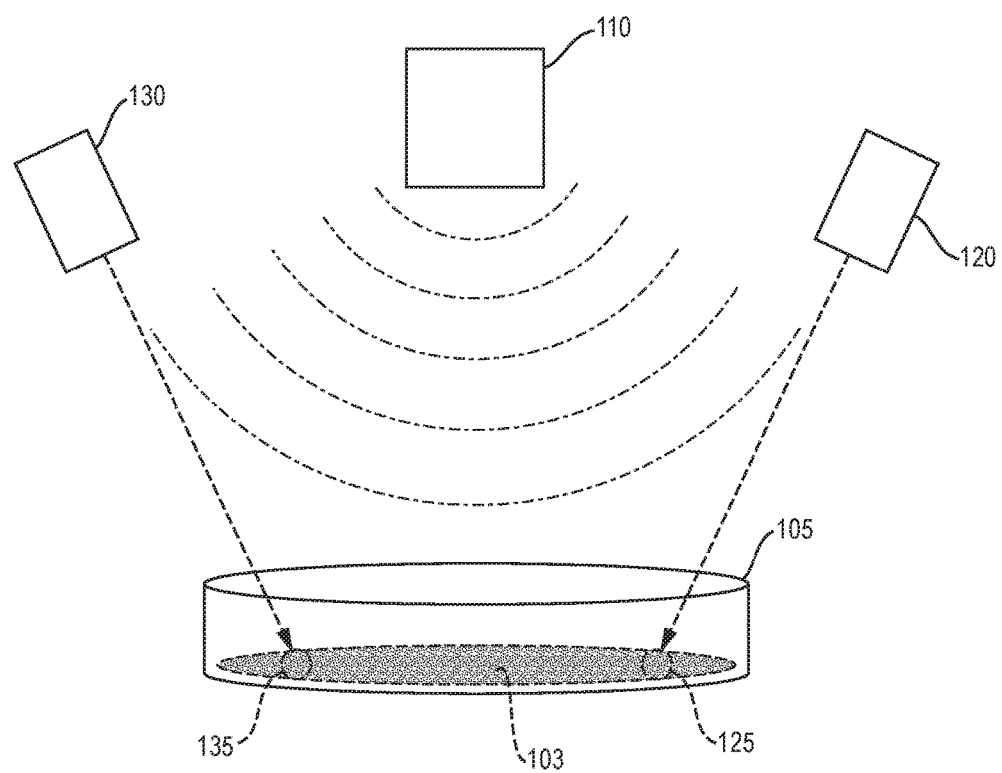

METHODS AND APPARATUS FOR SHIFTED-WAVELENGTH PHOTOSYNTHETIC ENERGY HARVESTING AND BIOMASS PRODUCTION

RELATED APPLICATIONS

This application claims the benefit of U.S. Provisional Application No. 62/321,878, filed Apr. 13, 2016 (the "Provisional Application"), the entire disclosure of which is herein incorporated by reference.

FIELD OF TECHNOLOGY

The present invention relates generally to photosynthesis.

BACKGROUND

A commonly held misconception is that the energy in infrared light is too low to drive photosynthesis for practical food production and biomass production. This misconception stems from the well-known fact that the higher the frequency of light, the greater the energy of the light photon, which is expressed in the relationship $E=hf$ (where $E$=energy of photon, $h$=Planck's constant, $f$=frequency of photon).

In this commonly held misconception, the wavelength (and thus energy) of the photons of incident light determines the amount of energy stored during photosynthesis (such as the amount of energy stored in bonds of the "energy carrier molecules", such as during cyclic photophosphorylation of ADP to ATP by PS-I or Z-Scheme involving PS-I and PS-II resulting in both ATP and NADPH).

This misconception is incorrect. For instance, a photon of blue light at 488 nm has about 30% more energy than a photon of red light at 633 nm. But, in fact, both photons may impart the same amount of energy when used by bacteriorhodopsins (bR), reaction centers (RC), photosystems-I-II (PS-I and -II) or any photosynthetic membrane protein-chromophore complexes.

This is because even though the absorption peaks of these photosynthetic molecular complexes vary, the absorption curves may be spread out over hundreds of nanometers and only the external action spectra efficiencies may be affected by the distribution of wavelengths of the source light while the internal quantum yields may depend on process pathways. (The number of O2 molecules evolved per incident photon is a hotly debated issue among scientists, with accepted values between ⅛ and 1/12) The photosynthetic process itself may be largely agnostic to the color of incident photons, depending instead on the total excess number of photons absorbed per unit area per unit time.

For instance, it is commonly held that green plants only absorb the red and blue parts of the solar spectrum rejecting the green due to the absorption spectrum peaks of ChlA and ChlB pigments. This is an explanation often given as to why plants appear mostly green. What is more, conventional schemes for efficient growth that are based on this understanding rely on using red and blue LEDs only.

In fact, photosynthesis may proceed just as well with any color of light in circumstances where the total number of co-incident photons absorbed per unit area per unit time does not fall below a photosynthetic threshold of 8-12 per photons absorbed in the time window corresponding to the relaxation characteristic time for PS-I and PS-II.

Of course, the organism may be sensitive to large fluxes of ultraviolet light (which is absorbed by both DNA and proteins causing damage) or to large fluxes of infrared light (which when absorbed by the water in the cytoplasm may elevate the temperature, causing damage by protein denaturation and errors in nucleic acid polymerization reactions).

It is worth noting that green photons alone may be sufficient to drive photosynthesis.

The abundant pigment-protein membrane complex photosystem-I (PS-I) is at the heart of the Earth's energy cycle. It is the central molecule in the "Z-scheme" of photosynthesis, converting sunlight into the chemical energy of life.

PS-I precisely orchestrates 96 chlorophyll molecules with electron donors and acceptors achieving efficient coherent energy transfer and near-unity charge separation quantum yield at ambient temperatures. This is a feat unmatched by any man-made photoelectronic device and has led to PS-I being studied as a candidate for many nanobioelectronic applications The energy for photosynthesis depends on photon flux gradients (number of photons per time per area going one way versus the other way). The absorption peaks of reaction centers and PS-I and PS-II are not tuned to harvest max $E=hf$ (or they'd be in the green); instead they're tuned to harvest max photon flux gradients.

SUMMARY

In illustrative implementations of this invention, light-harvesting complexes may be re-tuned to efficiently produce chemical energy at wavelengths shifted from sunlight.

In illustrative implementations of this invention, photosynthesis is driven by light at wavelengths shifted away from the absorption peaks of naturally-occurring light harvesting complexes (antennae complexes) and photosynthetic complexes. Instead of sunlight, high flux photon gradients with peaks in the infra-red (IR) or ultraviolet (UV) are used to drive the familiar primary energy conversion reactions. This shifted-wavelength photosynthesis, driven by IR or UV light, is employed to harvest energy and to produce biomass and biofuel.

In some implementations of this invention, genetic engineering or nanomaterial methods systematically shift and tune action spectra of light-driven membrane protein-chromophore complexes such as proton pumps, reaction centers and photosystems-I and -II. In some implementations, this wavelength-shifted photosynthesis is employed to grow biomass for food, biofuel and carbon capture by harvesting existent high-flux IR gradients that are produced by industrial waste heat exchangers or produced onboard sea, land, air or space vehicles. In some implementations, screening methods and apparatus are employed to discover high-yield conditions tuned to the specifics of the emission spectrum of each source and integrated extraction of shifted-wavelength photosynthesis products.

In some implementations of this invention, photosynthesis may occur due to absorption of UV or radio-wavelength photons. Without being limited by theory, this may occur because the directional flux gradient may matter, rather than the wavelength of individual photons.

The Summary and Abstract sections hereof: (a) do not limit this invention; (b) are intended only to give a general introduction to some illustrative implementations of this invention; (c) do not describe all of the details of this invention; and (d) merely describe non-limiting examples of this invention. This invention may be implemented in many other ways. Likewise, the description of this invention in the Field of Technology section is not limiting; instead it identifies, in a general, non-exclusive manner, a field of technology to which some implementations of this invention generally relate.

BRIEF DESCRIPTION OF THE DRAWINGS

The attached FIGURE shows apparatus for applying light of different frequencies to a colony of organisms.

The FIGURE shows an illustrative implementation of this invention. The example shown in the FIGURE does not limit this invention. This invention may be implemented in many other ways.

DETAILED DESCRIPTION

In some implementations of this invention, the absorption spectra of photosynthetic biomolecules in living cells may be tuned.

Purple bacteria, algae or other photosynthetic unicellular organisms may be screened microfluidically for survival in environments slowly adjusted to simulate the spectral distribution of the source.

In illustrative implementations, this screening may be done as follows:

The screening may start with a colony of naturally occurring organisms (e.g., all of one species of algae), confined in microfluidic microchannels.

Adaptive pressure may be applied favoring those individuals who survive longest to create the next colony. Additional mutagens targeted or random are applied and mutations that occur to the tuning regions of the complexes are monitored by DNA sequencing.

Tuning the peaks may be achieved by directed evolution using PACE, iterative site directed mutagenesis similar to that used by natural rhodopsins.

In some implementations of this invention, diversity of the organisms that are capable of wavelength-shifted photosynthesis may be increased via competition.

To develop organisms with shifted action spectra, the organisms may be exposed to light with dual peaks. High flux sources corresponding to their common trough (e.g. a green laser) may be applied to the organisms, thereby allowing for the survival of all the organisms. Also, a secondary source peaked at the desired wavelength—which may be either damaging (e.g. UV) or low-cross section (e.g. IR)—may also be applied to the organisms at controlled total fluxes (e.g. by modulating duration and frequency of pulses) such that the individual organisms that manage to get an advantage from harvesting the new source out-compete the ones who are surviving on high flux green. The adaptive pressure in this case favors survival of the outlier.

In illustrative implementations of this invention, the pulses of different wavelength may be applied at different spots on a contiguous population of algae. This configuration integrates the separation of populations with the selective pressure. In some cases: (a) the organisms are algae; (b) all of the algae are able to survive on global availability of high flux green; and (c) the off-peak UV and IR spots will have a lower average concentration of algae that cannot withstand these wavelengths and a higher concentration of those that adapted to be able to consume these wavelengths. In some implementations, dual differentiation occurs: accelerated depletion of the "normal" and sub-optimal green harvesters, low advantage to superoptimal green harvesters, enormous advantage to UV or IR harvesters who may be from a population of suboptimal green harvesters (which would not be discovered if adaptive pressure were applied globally).

There may be two added benefits for this approach: (1) Combining the members of UV and IR harvesters into one hybrid organism may be done by inserting the both genes by conventional transformation methods, or physical confinement to form syncytia, the stepping stone to multicellular complexity. (2) The local environment at the UV and IR spots may be constantly sampled by cells in various stages of their cycle, including during cell division. Synchronization of pulse trains with discrete events may be achieved by statistical ensemble. The mutagenesis and epigenetic postranslational and regulatory modifications that result in harvesters of desired action spectra may be tracked back to the known phases of cell growth and metabolism, including down to individual steps in the photosynthetic cascade. Iterative optimization may occur at very low overhead since (a) there is a large number of cells in different states and a large number of photons per pulse and (b) chirps and combs of pulses are may be produced in any combinations and permutations. Each successful pulse sequence may be tracked back to events and examined systematically.

For instance, pulses synchronized with metabolic circuit oscillations (that would never occur naturally for long enough to become adaptive pressures) may cause unexpected phenotypes to emerge.

In some implementations, "one-offs" are re-created inexpensively driving not only adaptation but also exaptation by screening vast numbers of conditions over practical timescales. In some implementations, each such finding is identifiable by an unambiguous pulse sequence that may be repeated exactly, over large scales (e.g. illuminating the entire petri instead of the spot) increasing the new population to numbers sufficient for standard sequencing analysis The attached FIGURE shows apparatus for applying light of different frequencies to a colony of organisms, in an illustrative implementation of this invention. In the example shown in the FIGURE, a colony of organisms 103 lives in a structure 105, such as a petri dish or one or more microfluidic channels. The structure 105 is configured such that light from a first light source 110, second light source 120 and third light source 130 may illuminate all or a portion of the colony of organisms 103. For example, the structure may include transparent walls or may include apertures through which light may pass.

In the example shown in the FIGURE, the first light source 110 may illuminate the entire structure 105, and thus may illuminate the entire colony of organisms 103, with high flux green light 115. A second light source 120 may emit pulses of UV (ultra-violet) light that illuminate only a small region 125 of the structure 105, and thus illuminate only a small portion of the colony of organisms 103. The second light source 120 may include one or more optical elements (such as lens, or mirrors) that focus the pulses of UV light on region 125, or may emit a narrow, pulsed beam of collimated pulsed UV light that strikes region 125. A third light source 130 may emit pulses of IR (infra-red) light that illuminate only a small region 135 of the structure 105, and thus illuminate only a small portion of the colony of organisms 103. The third light source 130 may include one or more optical elements (such as lens, or mirrors) that focus the pulses of IR light on region 135, or may emit a narrow, pulsed beam of collimated pulsed UV light that strikes region 135.

In some implementations of this invention, selection and screening of the organisms is achieved by partial blocking of a central peak of a photon source.

The most abundant solar photon is in the green with its range bound on both sides with absorbing pigments that have lowest cross sections where the retinol in eye and bacteriorhodopsin have their peaks. The green photon may excite the P680 and p700 directly but the yield for direct excitation is the lowest in a two-step scheme. This shows the Z-scheme relies on the absorption of four coincidental (2 for PS1 P700* and 2 for PS2 P680*) photons.

Note that the yield does not fall in the gap between the red and blue absorption peaks of Chl (where the green peak for sun and retinal is). To evolve a photosynthetic organism to harvest a high photon flux source, we may generate absorption peaks on either side of the source peak, which may be done by notch-filtering.

Non-limiting examples of use scenarios for this invention include: (a) growing biomass, such as aquaculture feed; and (b) producing biosolar electricity.

In some implementations of this invention, pond biomass is grown using wavelength-shifted photosynthesis. Then the products of the pond cultures are harvested, such as by separating the lysed algae biomass into materials for aquaculture feed, cosmetics, or nutrisupplements.

In some use scenarios of this invention, the infrared light for wavelength-shifted photosynthesis is produced by heat exchangers.

Computers

In illustrative implementations of this invention, one or more computers (e.g., servers, network hosts, client computers, integrated circuits, microcontrollers, controllers, field-programmable-gate arrays, personal computers, digital computers, driver circuits, or analog computers) are programmed or specially adapted to perform one or more of the following tasks: (1) to control the operation of, or interface with, one or more light sources; (2) to control the operation of, or interface with, one or more valves or pumps for controlling flow of fluid into or out of one or more structures (e.g., microfluidic channels or petri dishes) that contain living organisms; (3) to control the operation of, or interface with, one or more heaters or other devices for controlling physical conditions (such as temperature or moisture) in structures that contain living organisms; (4) to receive data from, control, or interface with one or more sensors; (5) to perform any other calculation, computation, program, algorithm, or computer function described or implied above; (6) to receive signals indicative of human input; (7) to output signals for controlling transducers for outputting information in human perceivable format; and (8) to process data, to perform computations, to execute any algorithm or software, and to control the read or write of data to and from memory devices (items 1-8 of this sentence referred to herein as the "Computer Tasks. The one or more computers may communicate with each other or with other devices either: (a) wirelessly, (b) by wired connection, (c) by fiber-optic link, or (d) by a combination of wired, wireless or fiber optic links.

In exemplary implementations, one or more computers are programmed to perform any and all calculations, computations, programs, algorithms, computer functions and computer tasks described or implied above. For example, in some cases: (a) a machine-accessible medium has instructions encoded thereon that specify steps in a software program; and (b) the computer accesses the instructions encoded on the machine-accessible medium, in order to determine steps to execute in the program. In exemplary implementations, the machine-accessible medium may comprise a tangible non-transitory medium. In some cases, the machine-accessible medium comprises (a) a memory unit or (b) an auxiliary memory storage device. For example, in some cases, a control unit in a computer fetches the instructions from memory.

In illustrative implementations, one or more computers execute programs according to instructions encoded in one or more tangible, non-transitory, computer-readable media. For example, in some cases, these instructions comprise instructions for a computer to perform any calculation, computation, program, algorithm, or computer function described or implied above. For example, in some cases, instructions encoded in a tangible, non-transitory, computer-accessible medium comprise instructions for a computer to perform the Computer Tasks.

Definitions

The terms "a" and "an", when modifying a noun, do not imply that only one of the noun exists. For example, a statement that "an apple is hanging from a branch": (i) does not imply that only one apple is hanging from the branch; (ii) is true if one apple is hanging from the branch; and (iii) is true if multiple apples are hanging from the branch.

The term "comprise" (and grammatical variations thereof) shall be construed as if followed by "without limitation". If A comprises B, then A includes B and may include other things.

The term "computer" includes any computational device that performs logical and arithmetic operations. For example, in some cases, a "computer" comprises an electronic computational device, such as an integrated circuit, a microprocessor, a mobile computing device, a laptop computer, a tablet computer, a personal computer, or a mainframe computer. In some cases, a "computer" comprises: (a) a central processing unit, (b) an ALU (arithmetic logic unit), (c) a memory unit, and (d) a control unit that controls actions of other components of the computer so that encoded steps of a program are executed in a sequence. In some cases, a "computer" also includes peripheral units including an auxiliary memory storage device (e.g., a disk drive or flash memory), or includes signal processing circuitry. However, a human is not a "computer", as that term is used herein.

"Defined Term" means a term or phrase that is set forth in quotation marks in this Definitions section.

For an event to occur "during" a time period, it is not necessary that the event occur throughout the entire time period. For example, an event that occurs during only a portion of a given time period occurs "during" the given time period.

The term "e.g." means for example.

The fact that an "example" or multiple examples of something are given does not imply that they are the only instances of that thing. An example (or a group of examples) is merely a non-exhaustive and non-limiting illustration.

Unless the context clearly indicates otherwise: (1) a phrase that includes "a first" thing and "a second" thing does not imply an order of the two things (or that there are only two of the things); and (2) such a phrase is simply a way of identifying the two things, respectively, so that they each may be referred to later with specificity (e.g., by referring to "the first" thing and "the second" thing later). For example, unless the context clearly indicates otherwise, if an equation has a first term and a second term, then the equation may (or may not) have more than two terms, and the first term may occur before or after the second term in the equation. A phrase that includes a "third" thing, a "fourth" thing and so on shall be construed in like manner.

"Fluid" means a gas or a liquid.

"For instance" means for example.

To say a "given" X is simply a way of identifying the X, such that the X may be referred to later with specificity. To say a "given" X does not create any implication regarding X. For example, to say a "given" X does not create any implication that X is a gift, assumption, or known fact.

"Herein" means in this document, including text, specification, claims, abstract, and drawings.

As used herein: (1) "implementation" means an implementation of this invention; (2) "embodiment" means an embodiment of this invention; (3) "case" means an implementation of this invention; and (4) "use scenario" means a use scenario of this invention.

The term "include" (and grammatical variations thereof) shall be construed as if followed by "without limitation".

"Light" means electromagnetic radiation of any frequency. For example, "light" includes, among other things, visible light, ultraviolet light and infrared light. Likewise, any term that directly or indirectly relates to light (e.g., "imaging") shall be construed broadly as applying to electromagnetic radiation of any frequency.

The term "or" is inclusive, not exclusive. For example, A or B is true if A is true, or B is true, or both A or B are true. Also, for example, a calculation of A or B means a calculation of A, or a calculation of B, or a calculation of A and B.

A parenthesis is simply to make text easier to read, by indicating a grouping of words. A parenthesis does not mean that the parenthetical material is optional or may be ignored.

As used herein, the term "set" does not include a group with no elements. Mentioning a first set and a second set does not, in and of itself, create any implication regarding whether or not the first and second sets overlap (that is, intersect).

Unless the context clearly indicates otherwise, "some" means one or more.

As used herein, a "subset" of a set consists of less than all of the elements of the set.

The term "such as" means for example.

"Visible light" means light that has a wavelength that is greater than or equal to 400 nm and less than or equal to 700 nm.

Except to the extent that the context clearly requires otherwise, if steps in a method are described herein, then the method includes variations in which: (1) steps in the method occur in any order or sequence, including any order or sequence different than that described; (2) any step or steps in the method occurs more than once; (3) any two steps occur the same number of times or a different number of times during the method; (4) any combination of steps in the method is done in parallel or serially; (5) any step in the method is performed iteratively; (6) a given step in the method is applied to the same thing each time that the given step occurs or is applied to different things each time that the given step occurs; (7) one or more steps occur simultaneously, or (8) the method includes other steps, in addition to the steps described herein.

This Definitions section shall, in all cases, control over and override any other definition of the Defined Terms. The Applicant or Applicants are acting as his, her, its or their own lexicographer with respect to the Defined Terms. For example, the definitions of Defined Terms set forth in this Definitions section override common usage or any external dictionary. If a given term is explicitly or implicitly defined in this document, then that definition shall be controlling, and shall override any definition of the given term arising from any source (e.g., a dictionary or common usage) that is external to this document. If this document provides clarification regarding the meaning of a particular term, then that clarification shall, to the extent applicable, override any definition of the given term arising from any source (e.g., a dictionary or common usage) that is external to this document. To the extent that any term or phrase is defined or clarified herein, such definition or clarification applies to any grammatical variation of such term or phrase, taking into account the difference in grammatical form. For example, the grammatical variations include noun, verb, participle, adjective, and possessive forms, and different declensions, and different tenses.

Variations

This invention may be implemented in many different ways. Here are some non-limiting examples:

In some implementations, this invention is a method comprising applying stimuli to a colony of organisms, such that (a) the stimuli include illuminating the colony with visible light and with light that has a wavelength that is outside of the range of wavelengths of visible light; and (b) the stimuli, taken together, tend to favor survival of organisms that are adapted to perform photosynthesis which involves absorbing energy from light that has a wavelength that is outside of the range of wavelengths of visible light. In some cases, the illuminating comprises (a) illuminating the entire colony of organisms with green light, (b) illuminating a first portion of the colony, but not a second portion of the colony, with ultraviolet light, and (c) illuminating the second portion of the colony, but not the first portion of the colony, with infrared light. In some cases, the infrared light is pulsed. In some cases, the ultraviolet light is pulsed. In some cases, the organisms comprise algae. In some cases, the organisms comprise bacteria. In some cases, the stimuli, taken together, cause selective breeding or mutation of the organisms, such that, after the stimuli are applied to multiple generations of the organisms, a majority of individual organisms in the colony are adapted to perform photosynthesis which involves absorbing energy from light that has a wavelength that is outside of the range of wavelengths of visible light. Each of the cases described above in this paragraph is an example of the method described in the first sentence of this paragraph, and is also an example of an embodiment of this invention that may be combined with other embodiments of this invention.

In some implementations, this invention is a system comprising: (a) one or more light sources; (b) one or more chambers; and (c) one or more computers; wherein (i) the one or more chambers are configured to contain a colony of organisms, (ii) the one or more computers are programmed to control the one or more light sources, such that the one or more light sources apply stimuli to the colony by illuminating the colony with visible light and with light that has a wavelength that is outside of the range of wavelengths of visible light, and (iii) the stimuli, taken together, tend to favor survival of organisms that are adapted to perform photosynthesis which involves absorbing energy from light that has a wavelength that is outside of the range of wavelengths of visible light.

In some implementations, this invention is an apparatus comprising: (a) one or more light sources; (b) one or more chambers; and (c) one or more computers; wherein (i) the one or more chambers are configured to contain a colony of organisms, and (ii) the one or more computers are programmed to control the one or more light sources, such that the one or more light sources apply stimuli to the colony by (A) emitting green light that illuminates the entire colony, (B) emitting ultraviolet light that (I) illuminates a first region of the structure containing a first portion of the colony but (II) does not illuminate a second region of the structure containing a second portion of the colony, and (C) emitting infrared light that (I) illuminates the second region of the structure containing the second portion of the colony but (II) does not illuminate the first region of the structure containing the first portion of the colony. In some cases, the one or more chambers each comprise one or more microfluidic channels. In some cases, the one or more chamber each comprise one or more petri dishes. In some cases, the one or more light sources each comprise one or more light emitting diodes. In some cases, the one or more light sources each comprise one or more lasers. In some cases, the one or more computers are programmed to control the one or more light sources, such that the stimuli are applied to multiple generations of the organisms. In some cases, the set of stimuli, taken together, cause selective breeding or mutation of the organisms such that, after the stimuli are applied to multiple generations of the organisms, a majority of individual organisms in the colony are adapted to perform photosynthesis that involves absorbing energy from light that has a wavelength that is outside of the range of wavelengths of visible light. Each of the cases described above in this paragraph is an example of the apparatus described in the first sentence of this paragraph, and is also an example of an embodiment of this invention that may be combined with other embodiments of this invention.

The above description (including without limitation any attached drawings and figures) describes illustrative implementations of the invention. However, the invention may be implemented in other ways. The methods and apparatus which are described herein are merely illustrative applications of the principles of the invention. Other arrangements, methods, modifications, and substitutions by one of ordinary skill in the art are therefore also within the scope of the present invention. Numerous modifications may be made by those skilled in the art without departing from the scope of the invention. Also, this invention includes without limitation each combination and permutation of one or more of the implementations (including hardware, hardware components, methods, processes, steps, software, algorithms, features, or technology) that are described or incorporated by reference herein.

What is claimed is:

1. A method comprising applying stimuli to a colony of organisms, such that:
   (a) the stimuli include illuminating the colony with visible light and with light that has a wavelength that is outside of the range of wavelengths of visible light; and
   (b) the stimuli, taken together, tend to favor survival of organisms that are adapted to perform photosynthesis which involves absorbing energy from light that has a wavelength that is outside of the range of wavelengths of visible light, wherein the illuminating comprises:
   (i) illuminating the entire colony of organisms with green light;
   (ii) illuminating a first portion of the colony, but not a second portion of the colony, with ultraviolet light; and
   (iii) illuminating the second portion of the colony, but not the first portion of the colony, with infrared light.

2. The method of claim 1, wherein the infrared light is pulsed.

3. The method of claim 1, wherein the ultraviolet light is pulsed.

4. The method of claim 1, wherein the organisms comprise algae.

5. The method of claim 1, wherein the organisms comprise bacteria.

6. The method of claim 1, wherein the stimuli, taken together, cause selective breeding or mutation of the organisms, such that, after the stimuli are applied to multiple generations of the organisms, a majority of individual organisms in the colony are adapted to perform photosynthesis which involves absorbing energy from light that has a wavelength that is outside of the range of wavelengths of visible light.

7. The method of claim 1, wherein the method is performed with an Apparatus comprising:
   (a) one or more light sources;
   (b) one or more chambers; and
   (c) one or more computers; wherein
   (i) the one or more chambers are configured to contain the colony of organisms, and
   (ii) the one or more computers are programmed to control the one or more light sources, such that the one or more light sources apply at least some of the stimuli to the colony by
   (A) emitting the green light that illuminates the entire colony,
   (B) emitting the ultraviolet light that illuminates the first portion of the colony but does not illuminate the second portion of the colony, and
   (C) emitting the infrared light that illuminates the second portion of the colony but does not illuminate the first portion of the colony.

8. The method of claim 7, wherein the one or more chambers each comprise one or more microfluidic channels.

9. The method of claim 7, wherein the one or more chambers each comprise one or more petri dishes.

10. The method of claim 7, wherein the one or more light sources each comprise one or more light emitting diodes.

11. The method of claim 7, wherein the one or more light sources each comprise one or more lasers.

12. The method of claim 7, wherein the one or more computers are programmed to control the one or more light sources, such that the stimuli are applied to multiple generations of the organisms.

13. The method of claim 12, wherein the set of stimuli, taken together, cause selective breeding or mutation of the organisms such that, after the stimuli are applied to multiple generations of the organisms, a majority of individual organisms in the colony are adapted to perform photosynthesis that involves absorbing energy from light that has a wavelength that is outside of the range of wavelengths of visible light.

* * * * *